United States Patent [19]

Nair

[11] Patent Number: 5,231,174

[45] Date of Patent: Jul. 27, 1993

[54] 2'ISODIDEOXY-β-D-NUCLEOSIDES AS STABLE ANTIVIRAL AGENTS

[75] Inventor: Vasu Nair, Iowa City, Iowa

[73] Assignee: University of Iowa Research Foundation, Oakdale, Iowa

[21] Appl. No.: 843,913

[22] Filed: Feb. 27, 1992

[51] Int. Cl.$^5$ .................. C07H 19/067; C07H 19/10; C07H 19/173; C07H 19/20

[52] U.S. Cl. ..................................... 514/46; 536/26.7; 536/27.14; 514/43; 514/45; 514/47; 514/48; 514/49; 514/50; 514/51

[58] Field of Search ............... 536/23, 24, 26; 514/45, 514/46, 49, 50

[56] References Cited

U.S. PATENT DOCUMENTS

| | | | |
|---|---|---|---|
| 4,115,555 | 9/1978 | Wade et al. | 514/43 |
| 4,713,372 | 12/1987 | Schaumberg et al. | 514/45 |
| 4,724,232 | 2/1988 | Rideout et al. | 514/50 |
| 4,861,759 | 8/1989 | Mitsuya et al. | 514/46 |
| 4,873,228 | 10/1989 | Schmalzl et al. | 514/49 |
| 4,879,277 | 11/1989 | Mitsuya et al. | 514/49 |
| 4,880,782 | 11/1989 | Eckstein et al. | 514/45 |
| 4,918,056 | 4/1990 | Bobek et al. | 514/25 |
| 4,990,498 | 2/1991 | Suhadolnik | 514/47 |
| 4,997,818 | 3/1991 | McCaffrey et al. | 514/45 |
| 5,026,687 | 6/1991 | Yarchoan et al. | 514/45 |
| 5,028,595 | 7/1991 | Soo | 514/49 |
| 5,039,667 | 8/1991 | Tyrrell et al. | 514/45 |

FOREIGN PATENT DOCUMENTS 0286028 10/1988 European Pat. Off. .
0371366 6/1990 European Pat. Off. .

OTHER PUBLICATIONS

Crane et al., "Isonucleosides from Glucosamine," *J. Carbohydrates Nucleosides Nucleotides*, 7(5), 281-296 (1980).

Doboszewski et al., "Synthesis of C-Nucleoside Analogues of 2',3'-Dideoxycytidine, 3'-Azido-2',3'-dideoxyuridine (CS-87), and 2',3'-dideoxy-2',3'-didehydrocytidine," *J. Org. Chem.*, 53, 2777-2782 (1988).

Chu et al., "Structure-Activity Relationships of Pyrimidine Nucleosides as Antiviral Agents for Human Immunodeficiency Virus Type I in Peripheral Blood Mononuclear Cells," *J. Med. Chem.*, 32, 612-617 (1989).

Frank et al., "Anabolism and Mechanisms of Action of Ro24-5098, an Isomer of 2',3'-Dideoxyadenosine (ddA) with Anti-HIV Activity", Annals New York Academy of Sciences 1990, 616, 408.

Primary Examiner—Johnnie R. Brown
Assistant Examiner—L. Eric Crane
Attorney, Agent, or Firm—Zarley, McKee, Thomte, Voorhees & Sease

[57] ABSTRACT

The present invention is concerned wtih new 2'-isomeric 2 2',3'-dideoxy-2'β-D-nucleosides and their derivatives where the base moiety has β-stereochemistry but is transposed from the normal 1'-position to the 2'-position and the carbohydrate moiety has the D-configuration at the 4'-position. These compounds are resistant towards hydrolytic cleavage of the glycosidic bond and are resistant to enzymatic deamination. They have potential in the treatment or prophylaxis of viral infections, particularly retroviral infections and especially AIDS.

8 Claims, No Drawings

2'ISODIDEOXY-β-D-NUCLEOSIDES AS STABLE ANTIVIRAL AGENTS

GRANT REFERENCE

This invention was made with government support under contract number AI-29842 awarded by the National Institutes of Health. The government has certain rights in the invention.

BACKGROUND OF THE INVENTION

Acquired Immune Deficiency Syndrome (AIDS) has become recognized as one of the most catastrophic diseases to confront humanity. The etiologic agent of this disease is a lymphotrophic retrovirus referred to as human immunodeficiency virus (HIV-1) (Fauci, *Science*, 1988, 239. 617). Other retroviruses related to HIV-1 are also being identified. A few synthetic modified nucleosides have shown some promise in studies involving AIDS or AIDS-related complex (ARC) (Mitsuya et al, *Proc. Natl. Acad. Sci. USA*, 1985, 82. 7096; 1986, 83. 1911; DeClercq, *J. Med. Chem.*, 1986, 29. 1561, Nair et al, *J. Am. Chem. Soc.*, 1989, 111. 8502; Yarchoan et al, *Science*, 1989; 245. 412, Mitsuya et al, *Science*, 1990, 249, 1533). These include 3'-azido-3'-deoxythymidine (AZT), 2',3'-dideoxycytidine (ddC), 2',3'-dideoxyadenosine (ddA), and 2',3'-dideoxyinosine (ddI). The antiviral activity of these compounds is associated with their ability to inhibit, in their phosphorylated triphosphate forms, a key enzyme in the virus life cycle, i.e. reverse transcriptase (Mitsuya et al, *Proc. Natl. Acad. Sci. USA*, 1987, 84. 2033). According to Broder and coworkers (*Biochem. Pharmacol.*, 1987, 36 1765), ddA is superior to ddC and AZT in terms of therapeutic index. However, the therapeutic efficacy of ddA is limited by its instability, both with respect to rapid enzymatic deamination by the ubiquitous mammalian enzyme, adenosine deaminase, and hydrolytic cleavage of the glycosidic bond (Balzarini et al, *Biochem. Biophys. Res. Commun.*, 1987, 145. 277; Nair et al, *J. Org. Chem.* 1990, 55. 3695. Other anti-HIV active dideoxynucleosides also suffer from the disadvantage of hydrolytic instability. There is, therefore, a critical need for the development of dideoxynucleosides with anti-HIV activity but with greater hydrolytic and enzymatic stability than ddA and other dideoxynucleosides.

The primary objective of the present invention is to provide dideoxynucleosides with anti-HIV activity with increased hydrolytic and enzymatic stability in comparison with ddA and other dideoxynucleosides.

Another objective of the present invention is to provide pharmaceutical compositions which contain compounds of the present invention in a hydrolytically and enzymatically stable environment, and which can be used as effective non toxic antiviral treating agents.

The yet further objective of the present invention is to provide a method of preparation of the compounds of the present invention and the pharmaceutical compositions of the present invention.

The objective of the present invention disclosure is concerned with the development of a series of new 2'-isodideoxy-β-D-nucleosides and their derivatives that are hydrolytically very stable so that they would have enhanced therapeutic potential as antiviral agents, in particular as anti-HIV agents.

A further objective is to provide effective and direct routes to the synthesis of these isodideoxy-D-nucleosides and their derivatives.

A still further objective of the present invention is to provide therapeutic compositions containing the stable compounds of this invention.

The method and manner of accomplishing each of the above objectives of the invention will become apparent from the detailed description as set forth below.

SUMMARY OF THE INVENTION

The present invention is concerned with new 2'-isomeric 2',3'-dideoxy-2'-β-D-nucleosides and their derivatives where the base moiety has β-stereochemistry but is transposed from the normal 1'-position to the 2'-position and the carbohydrate moiety has the D-configuration at the 4'-position. These compounds are resistant towards hydrolytic cleavage of the glycosidic bond and are resistant to enzymatic deamination. They have potential in the treatment or prophylaxis of viral infections, particularly retroviral infections and especially AIDS.

DETAILED DESCRIPTION OF THE INVENTION

The present invention relates to a new class of optically active dideoxynucleosides where the base moiety has β-stereo-chemistry but is transposed from the 1'-to the 2'-position and where the carbohydrate moiety has the D-configuration These compounds are structurally different from and optical isomers of those described by Huryn et al (European Pat. Office No. 0 383 239, 2/12/1990) and their D-configuration is the same stereochemistry found in natural ribonucleosides and deoxyribonucleosides. These isomeric dideoxynucleosides are hydrolytically much more stable than the "normal" dideoxynucleosides (e.g. ddA, ddC) and there is evidence to suggest that they may have potent anti-HIV activity.

This invention relates to a series of synthesized 2-isodideoxy-β-D-nucleosides with potential as anti-AIDS treatment compounds for which the general structure may be represented by the following formulas (I, II, III):

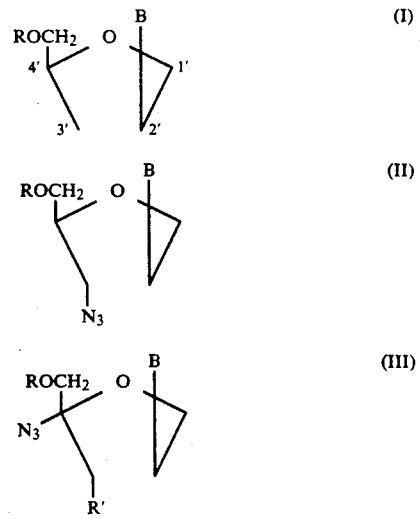

In the above formula (I), the base moiety (B) has β-stereochemistry and is at the 2'-position of the dideoxy carbohydrate component. This base moiety may be generally described as being adenine, hypoxanthine, guanine, cytosine, uracil, thymine and other 5-substituted pyrimidines containing small functional groups at the 5-position (e.g. 5-ethyl, 5-alkenyl, 5-alkynyl, 5-fluoro). The absolute stereochemistry at the 4'-position of the carbohydrate moiety is D (i.e. the $CH_2OR$ group at the 4'-position is $\beta$ and has a cis relationship to the base moiety "B"). The OR group may be hydroxyl (OH), O-acyl (e.g. acetate), or phosphorylated group (e.g. H-phosphonate [-O-PH(O)OH]). Other derivatives of this new family of compounds include the 3'-azido and 4'-azido compounds of the formulas II and III, respectively, where the base moiety (B) is thymine or uracil and OR is hydroxyl (OH), O-acyl group (e.g. acetate), or phosphorylated group (e.g. H-phosphonate [-O-PH(O)OH]), and R' = H or OH.

These compounds can be prepared using efficient and fairly straightforward syntheses. A common precursor for the synthesis of these compounds is 1,4-anhydro-5-O-benzoyl-3-deoxy-2-O-p-toluenesulfonyl-D-ribitol which can be prepared from 5-O-benzoyl-3-deoxy-D-ribose (Nair et al, *J. Am. Chem. Soc.* 1977, 99. 1571; De Bernardo et al, *J. Org. Chem.* 1985, 50. 3457) by deoxygenation of the hydroxyl group at the 1-position, via its methyl acetal (Benneck et al, *J. Org. Chem.* 1987, 52. 892) followed by tosylation of the 2-hydroxyl group. Coupling of the resulting tosylate with the bases adenine, thymine and cytosine in N,N-dimethylfuran (DMF) in the presence of $K_2CO_3$ and 18-crown-6 gave, after deprotection, the corresponding 2'-isodideoxy-$\beta$-D-nucleosides. The cytidine analog was prepared in several steps from the uracil analog, through the triazole approach (Sung, *Chem. Commun.* 1981, 11. 1089). The 3'-$\beta$-azido analogs of this family of compounds where the base moiety is either thymine or uracil were prepared from the corresponding protected 1'-deoxy-2'-isonucleoside 3'-$\beta$-mesylate by azide displacement followed by deprotection. The 4'-$\alpha$-azido analogs of this family where the base moiety is either thymine or uracil and the carbohydrate moiety has an $\alpha$-hydroxy group or hydrogen at the 3'-position were prepared from the appropriate 2'-isonucleoside by introduction of the azido group at the 4'-position via the corresponding 4'-alkenyl compound using an approach related to that described by Prisbe et al (European Pat. Office No. 0 371 366, 11/20/89). The 5'-O-acyl and 5'-phosphorylated derivatives (e.g. H-phosphonates) were prepared by established procedures well known to those of ordinary skill in the art. The structure and absolute stereochemistry of the intermediates and target compounds were confirmed by a combination of multinuclear high-field NMR and ultraviolet spectra, single crystal X-ray data, elemental analyses and chemical methods (e.g. formation of 2,5'-anhydro nucleosides).

Glycosidic bond stability studies were carried out at acidic pHs using differential UV spectroscopy. The procedures have been previously described by us (Nair et al, *J. Org. Chem.* 1990, 55. 3695). Unlike the known dideoxynucleosides with the base moieties at the 1'-position, the 2'-isodideoxy-D-nucleosides described herein were found to be very stable with respect to glycosidic bond cleavage. For example, 2-(6-amino-9H-purin-9-yl)-1,4-anhydro-2,3-dideoxy-D-arabinitol had a half life ($t_{\frac{1}{2}}$) of >16 days at pH 1. In comparison, the anti-HIV active 2',3'-dideoxyadenosine (ddA) has a half life ($t_{\frac{1}{2}}$) of <<1 hr at pH 3. The pyrimidine isodideoxy-$\beta$-D-nucleosides, like their purine counterparts, were also found to be very stable to hydrolysis even under strongly acidic conditions (e.g. 1,4-anhydro-2,3-dideoxy-2-[3,4-dihydro-2,4-dioxo-5-methyl-1(2H)-pyrimidinyl]-D-arabinitol was hydrolytically stable for many days at pH 1).

Stability studies with respect to hydrolytic deamination by mammalian enzymes in the case of adenine and cytosine containing isodideoxynucleosides were also considered. 2',3'-Dideoxyadenosine is readily deaminated by mammalian adenosine deaminase. In stark contrast, the invention compound, 2-(6-amino-9H-purin-9-yl)-1,4-anhydro-2,3-dideoxy-D-arabinitol, is almost totally resistant to hydrolytic deamination by mammalian adenosine deaminase (0.0010% of the activity of adenosine and 0.0017% of the activity of ddA). Because 2',3'-dideoxycytidine is not deaminated by cytidine deaminase (Cooney et al, *Biochem. Pharmacol.* 1986, 35. 2065) and because deamination requires the presence of the 3'-hydroxyl group (Kreis et al, *Helv. Chim. Acta,* 1978, 61. 1011), 2-[4-amino-2-oxo-1(2H)-pyrimidinyl]-1,4-anhydro-2,3-dideoxy-D-arabinitol would not be deaminated by mammalian cytidine deaminase.

Another aspect of the invention provides pharmaceutical compositions comprising one of the therapeutically active antiviral agents of the present invention or a pharmaceutically acceptable salt thereof, together with a pharmaceutically acceptable carrier therefor. In a particular aspect, pharmaceutical compositions comprise a compound of the present invention in an effective unit dosage form.

As used herein the term "effective unit dosage" or "effective unit dose" is denoted to mean a predetermined antiviral amount sufficient to be effective against the viral organism in vivo. Pharmaceutically acceptable carriers are materials useful for the purpose of administering the medicament, and may be solid, liquid or gaseous materials, which are otherwise inert and medically acceptable and are compatible with the active ingredients.

These pharmaceutical compositions may be given parenterally, orally, used as a suppository or pessary, applied topically as an ointment, cream, aerosol, powder, or given as eye or nose drops, depending on whether the preparation is used to treat internal or external viral infections.

For internal infections the compositions are administered orally or parenterally at dose levels, calculated as the free base, of about 0.1 to 250 mg per kg, preferably 1.0 to 50 mg per kg, or mammal body weight, and are used in man in a unit dosage form, administered a few times daily in the amount of 1 to 250 mg per unit dose.

For oral administration, fine powders or granules may contain diluting, dispersing and/or surface active agents, and may be presented in a draught, in water or in a syrup; in capsules or sacnets in the dry state or in a non-aqueous solution or suspension, wherein suspended agents may be included; in tablets, wherein binders and lubricants may be included; or in a suspension in water or a syrup. Where desirable or necessary, flavoring, preserving suspending, thickening or emulsifying agents may be included. Tablets and granules are preferred and these may be coated.

For parenteral administration or for administration as drops, the compounds may be presented in an aqueous solution in a concentration from about 0.1% to about 7%, most preferably from about 0.2% on a weight- /volume basis. This solution may contain antioxidants, buffers, etc.

The following examples are offered to illustrate but not limit the invention.

In the examples, the reported melting points are uncorrected and were determined on a Thomas-Hoover melting point apparatus fitted with a microscope. Nuclear magnetic resonance spectra were recorded on a Bruker Models AC-300 and WM360 pulse Fourier transform spectrometers. Mass spectra were determined on a VG TRIO single quadrupole GC/MS system or a VG Analytical Model ZAB-HF instrument with high-resolution FAB capability. Ultraviolet spectra were recorded and enzymatic studies and hydrolytic stability studies were done on a Varian Cary Model 3 or a Gilford Response spectrophotometer. Infrared spectra were recorded on an IBM Model 98 Fourier transform instrument. Lyophilizations were performed with a Virtis freezemobile 3 unit. Preparative layer chromatography plates were prepared by coating six 20 cm ×20 cm plates with a slurry made from 150 g of E. Merck $PF_{254}$ silica gel in 400 ml of water. The silica gel plates were allowed to dry slowly and were then activated for 3 h at 135° C. Flash chromatography was carried out using glass columns packed with 230-400 mesh silica gel. High performance liquid chromatography was done using Altex columns packed with Amberlite XAD-4 resin (Rohm and Haas) which was ground and sieved to 40-60 μm. Samples were injected with a gas tight syringe through an Altex 4-way slide valve. Separations were carried out at 20-80 psi using an FMI RRPSY-SS ¼ inch piston pump. Fractions were monitored by a Pharmacia UV-2 ultraviolet monitor and products were collected on a Gilson FC-100 fraction collector. Analytical and preparative HPLC separations were also carried out with a Waters automated 600E system with photodiode array detector and FOXY fraction collector using Delta-Pak $C_{18}$ and Hamilton PRP-1 columns. X-ray crystallographic data were obtained using an Enraf-Nonius CAD-4 diffractometer. Satisfactory elemental analyses were obtained for target compounds and were performed at Galbraith Laboratories, Inc., Knoxville, Tenn.

EXAMPLE 1

2-(6-Amino-9H-purin-9-yl)-1,4-anhydro-2,3-dideoxy-D-arabinitol 1,4-Anhydro-5-O-benzoyl-3-deoxy-2-O-p-toluenesulfonyl-D-ribitol was prepared from 5-benzoyl-3-deoxy-1,2-O-isopropylidene-α-D-ribofuranose by conversion to 5-O-benzoyl-3-deoxy-1-methoxy-α(β)-D-ribofuranose with methanolic HCl, demethoxylation of the latter followed by tosylation of the 2-position with tosyl chloride and pyridine. A mixture of adenine (0.354 g, 2.62 mmol), potassium carbonate (0.362 g, 2.62 mmol), 18-crown-6(0.347 g, 1.31 mmol), and 1,4-anhydro-5-O-benzoyl-3-deoxy-2-O-p-toluenesulfonyl-D-ribitol in DMF (11 mL) was stirred at 75° C. for 11 h. The solvent was removed under reduced pressure. The residue was purified by flash chromatography with 5% MeOH/CHCl$_3$ and afforded 0.269 g (0.793 mmol, 60.5%) of the 5'-benzoate of the title compound as a white solid: mp 193°-195° C.; $^1$H NMR (CDCl$_3$): δ2.13-2.22 (m,1H),2.74-2.84 (m,1H),4.12(dd,1H),4.29(dd,1H),4.39-4.50(m,2H),4.59(-dd,1H),5.32(m,1H),6.00(s,2H),7.40(t,2H),7.53(t ,1H),7.98(d,1H),8.02(s1H),8.31(s,1H); UV(MeOH) $\lambda_{max}$260 nm.

To a solution of the aforementioned product (0.106 g, 0.312 mmol) in methanol (15 mL), was added sodium methoxide (0.025 g, 0.462 mmol). After stirring for 2 h at room temperature, the reaction mixture was neutralized by stirring with Dowex ion-exchange resins (H+form) The resin was filtered and the filtrate was then concentrated under reduced pressure. The residue was purified on silica gel plates with 10% methanol/chloroform. Final purification by reversed-phase HPLC on Amberlite XAD-4 resin using 10% ethanol/water as the eluting solvent afforded the title compound 0.063 g(0.268 mmol, 85%) as a white solid mp: 152°-154° C.; $^1$H NMR(Me$_2$SO-d$_6$): δ2.09(m,1H),2.58(m,1H),3.55(m,2H),3.99(m,3H),4.95(-M,1H)5.17(m,1 H),7.25(s,2H),8.15(s,1H),8.26(s,1H); $^{13}$CNMR(Me$_2$SO-d$_6$): δ33.9,53.9,62.4,71.8,79.6,118.7,138.9,149.3,152.3,155.9; UV(H$_2$O)$\lambda_{max}$260nm(13,788);[α]$_d$=(−)26.6(c=0.27-,MeOH); mass spectrum,m/z 235(M+). The absolute stereochemistry was confirmed by X-ray crystallographic data.

EXAMPLE 2

2-(2-Amino-1,6-dihydro-6-oxo-9H-purin-9-yl)-1,4-anhydro-2,3-dideoxy-D-arabinitol A mixture of 2-amino-6-chloropurine (0.099 g, 0.58 mmol), potassium carbonate (0.017 g, 0.77 mmol), 18-crown-6 (0.062 g, 0.23 mmol) and 1,4-anhydro-5-O-benzoyl-3-deoxy-2-O-p-toluenesulfonyl-D-ribitol (0.146 g, 0.39 mmol) in DMF (7 mL) was stirred at 70° C. for 12 h. The solvent was removed under reduced pressure. The residue was purified by flash chromatography using 5% methanol/chloroform as eluting solvent to afford 0.078 g (0.21 mmol, 54%) of 1,4-anhydro-5-0-benzoyl-2-(6-chloro-9H-purin-9-yl)-2,3-dideoxy-D-arabinitol as a colorless viscous oil: $^1$H NMR (CDCl$_3$): δ2.08(m,1H), 2.65(m,1H), 4.01(dd,1H),4.18(dd,1H),4.31(m,1H),4.46(m,2H),5.04(-m,1H),5.60 s,2H),7.30(t,2H),7.43(t,2H),7.86(m,3H); UV(MeOH)$\lambda_{max}$247,310 nm.

A solution of the aforementioned protected nucleoside (0.065 g, 0.17 mmol) in MeOH(6mL) was cooled down to 0° C. and saturated with gaseous ammonia. The reaction mixture was allowed to stand at 0° C. for 2 h and then at room temperature for 22 h. Excess ammonia was purged out with nitrogen and the solvent was removed under reduced pressure. The residue was purified on a silica gel plate using 10% methanol/chloroform as eluting solvent. The band at R$_f$0.2 afforded 0.024 g (0.09 mmol, 52%) of 2-(2-amino-6-chloro-gH-purin-9-yl)-1,4-anhydro-2,3-dideoxy-D-arabinitol as a white solid: mp: 194°-196° C.; $^1$H NMR(Me$_2$SO-d$_6$): δ2.04(m,1H),2.5(m,1H),3.50-3.67(m,2H),3.-88-4.11(m,3H),4.94(m,1H),5.02(m,1H),6.91(s,2H),8.25(-s,1H); UV(MeOH): $\lambda_{max}$247 nm($\epsilon$5,596),309nm($\epsilon$6,313).

o A solution of the aforementioned 5'-deprotected nucleoside (0.043 g,0.16 mmol) in 1N NaOH(11mL) was stirred at 95° C. for 45 minutes. The reaction mixture was then neutralized with 1N acetic acid. Removal of the solvent under reduced pressure and purification of the residue by reversed-phase HPLC on Amberlite XAD-4 using 4% ethanol/water as eluting solvent afforded 0.028 g (0.11 mmol, 69%) of the title compound as a white solid: mp 261°-263° C.; $^1$H NMR (Me$_2$SO-d$_6$): δ1.97(m,1H),2.5(m,1H),3.52(m,2H),3.91(m,3H),4.91(m,2H),6.45(s,2 H),7.81(s,1H),10.6(s,1H); UV(H$_2$O)λ$_{max}$252 nm(ε11,583); 271 nm,sh(ε8,320); [α]$_D$ =(−)27° (c=0.22,MeOH).

EXAMPLE 3

1,4-Anhydro-2,3-dideoxy-2-(1,6-dihydro-6-oxo-9H-purin-9-yl)-D-arabinitol

A mixture of 6-chloropurine (0.162 g, 1.05 mmol), potassium carbonate (0.193 g, 1.4 mmol), 18-crown-6 (0.111 g, 0.42 mmol), and 1.4-anhydro-5-0-benzoyl-3-deoxy-2-0-p-toluenesulfonyl-D-ribitol (0.262 g, 0.7 mmol) in DMF (10 mL) was stirred at 75° C. for 14 h. The solvent was removed under reduced pressure and the residue was purified by flash chromatography with 5% methanol/chloroform to afford the protected nucleoside 0.090 g (0.25 mmol, 36%) as a white solid: mp 125°-127° C. A suspension of this nucleoside (0.085 g, 0.24 mmol) in 1N NaOH(15 mL) was stirred at 95° C. for 1 h and then neutralized with 1N acetic acid. The solvent was removed under reduced pressure. Purification of the residue by reversed-phase HPLC on Amberlite XAD-4 resin using 8% ethanol/water as eluting solvent afforded the title compound (0.021 g, 0.09 mmol, 38%) as a white solid: mp 98° C.; $^1$H NMR (Me$_2$SO-d$_6$): δ2.05 (m,1H),2.5(m,1H),3.58(dd,2H),3.97 (m,3H), 4.94(m,1H),5.15(m,1H),8.02(s,1H),8.16(s,1H); UV(H$_2$O) λ$_{max}$249 nm(ε10,027); [α]$_D$ =(−)27° (c=0.092,MeOH); mass spectrum, m/z 236(M$^+$).

EXAMPLE 4

1,4-Anhydro-2,3-dideoxy-2-[3,4-dihydro-2,4-dioxo-1(2H)-pyrimidinyl]-D-arabinitol A mixture of uracil (0.129 g, 1.15 mmol), potassium carbonate (0.212 g, 1.53 mmol), 18-crown-6 (0.405 g, 1.53 mmol) and 1,4-anhydro-5-0-benzoyl-3-deoxy-2-0-p-toluenesulfonyl-D-ribitol (0.289 g, 0.76 mmol) in DMF (4.2 mL) was stirred at 75° C. for 14 h. The solvent was removed under reduced pressure and the residue was purified by flash chromatography using 5 % methanol/chloroform as eluting solvent to afford 0.104 g (0.33 mmol, 43%) of the protected nucleoside as a white solid; mp 154°-156° C. A solution of this nucleoside (0.140 g, 0.44 mmol) in MeOH (10 mL) was cooled down to 0° C. and saturated with ammonia. The reaction mixture was allowed to stand at 0° C. for 2 h and then at room temperature for 46 h. Excess ammonia was purged out with nitrogen and then the solvent was removed under reduced pressure. The residue was purified on silica gel plates with 10% methanol/chloroform to afford 0.055 g (0.26 mmol, 59%) of the title compound as a white hygroscopic solid: $^1$H NMR (Me$_2$SO-d$_6$): δ1.73 (m,1H),2.42(m,1H),3.52(dd,2H),3.72-3.90(m,3H),4.91(m,1H),5.09(m,1H),5.58(d,J=8Hz,1H),7.72(d,J=8 Hz,1H),11.23(s,1H); UV(H$_2$O)λ$_{max}$266 nm(ε8,786);FTIR(KBr) 1682 cm$^{-1}$; [α]$_D$ =(+)31° (c=0.125,MeOH); mass spectrum, m/z 212(M$^+$).

EXAMPLE 5

1,4-Anhydro-2,3-dideoxy-2-[3,4-dihydro-2,4-dioxo-5-methyl-1(2H)-pyrimidinyl]-D-arabinitol A mixture of thymine (0.142 g, 1.12 mmol), potassium carbonate (0.208) g, 1.5 mmol), 18-crown-6(0.119 g, 0.45 mmol) and 1,4-anhydro-5-O-benzoyl-3-deoxy-2-O-p-toluenesulfonyl-D-ribitol (0.283 g, 0.75 mmol) in DMF (5 mL) was stirred at 75° C. for 14 h. The solvent was removed under reduced pressure. The residue was purified by flash chromatography using 5% methanol/chloroform as the mobile phase to afford 0.074 g (0.224 mmol, 30%) of the protected isothymidine. To a solution of this nucleoside (0.074 g, 0.22 mmol) in methanol (3.5 mL), was added sodium methoxide (0.018 g, 0.33 mmol). After stirring for 2 h at room temperature, the reaction mixture was neutralized with 5N acetic acid (2 drops). The solvent was removed under reduced pressure and the residue was purified on a silica gel plate with 10% methanol/chloroform to afford the title compound (0.18 mmol, 82%) as a very hygroscopic white solid: $^1$H NMR (Me$_2$SO-d$_6$): δ1.76 (m,4H),2.35(m,1H),3.45-3.52(m,1H),3.65(m,1H),3.72-3.87(m,3H),4.95(t,1H),5.1(m,1H),7.61(s,1H),11.21(s,1H; UV(MeOH)λ$_{max}$271 nm(ε9,554); [α]$_D$ =(+)26° (c=0.2,MeOH): FTIR(KBr)1670 cm$^{-1}$; mass spectrum, m/z 226(M+).

EXAMPLE 6

2-[4-Amino-2-oxo-1(2H)-pyrimidinyl]-1,4-anhydro-2,3-dideoxy-D-arabinitol

To a stirred solution of 1,4-anhydro-5-O-benzoyl-2,3-dideoxy-2-[3,4-dihydro-2,4-dioxo-1(2H)-pyrimidinyl]-D-arabinitol (0.187 g, 0.59 mmol) in pyridine (7 mL) was added 4-chlorophenylphosphorodichloridate (0.2 mL, 1.2 mmol) dropwise at 0° C. After the addition, 1,2,4-triazole (0.163 g, 2.36 mmol) was added to the reaction mixture which was then stirred at room temperature for 26 h. The solvent was removed under reduced pressure and the residue was taken up in dichloromethane and washed with water (3×25 mL). The organic portion was dried (Na$_2$SO$_4$), concentrated and purified on a silica gel plate with 6% methanol/chloroform to afford 0.101 g (0.27 mmol, 46%) of the 4-triazolo derivative of the starting nucleoside as a viscous yellow oil. A solution of this triazolo nucleoside (0.098 g, 0.27 mmol) in 1:6(v/v) of ammonium hydroxide/dioxane (4 mL) was stirred at room temperature for 14 h. The solvent was removed under reduced pressure and the residue was purified on a silica gel plate with 8% MeOH/CHCl$_3$ to afford 0.056 g (0.18 mmol, 66%) of 2-[4-amino-2-oxo-1(2H)-pyrimidinyl]-1,4-anhydro-5-0-benzoyl-2,3-dideoxy-D-arabinitol as a colorless viscous oil. To a solution of this nucleoside (0.056 g, 0.18 mmol) in methanol (3 mL) was added sodium methoxide (0.019 g, 0.35 mmol). The reaction mixture was stirred at room temperature for 1.5 h and then neutralized with 3M HCl (12 drops). Removal of solvent under reduced pressure and purification of the residue by reversed-phase HPLC on Amberlite XAD-4 using 4% ethanol/water as the eluting solvent afforded 0.014 g, (0.07 mmol, 39%) of the title compound as a white hygroscopic solid: $^1$H NMR (Me$_2$SO-d$_6$) δ1.67 (m,1H),2.38(m,1H),3.50(dd,2H),3.81(m,3H), 4.85(m,1H), 5.14(m.1H),5.68(d,J=7.1Hz,1H),7.02(s,2H), 7.68(d,J=7.1Hz,1H); 13CNMR(Me$_2$SO-d$_6$) δ33.9,55.0,62.3,71.9, 79.7, 94.0,142.3, 155.7, 165.3; UV(H$_2$O)λ$_{max}$274 nm(ε9,040); FTIR(KBr)1652cm$^{-1}$; [α]$_D$ =(+)87° (c=0.144,MeOH); mass spectrum,m/z 211 (M+).

EXAMPLE 7

5-O-acetyl-2-(6-amino-9H-purin-9-yl)-1,4-anhydro-2,3-dideoxy-D-arabinitol

Representative Example

To a suspension of 2-(6-amino-9H-purin-9-yl)-1,4-anhydro-2,3-dideoxy-D-arabinitol (0.029 g, 0.12 mmol) and 4-dimethylaminopyridine (0.001 g, 0.008 mmol) in anhydrous acetonitrile (2.5 mL), triethylamine (0.03 mL, 0.21 mmol) and acetic anhydride (0.014 mL, 0.15 mmol) were added. The reaction mixture was stirred at room temperature for 23 min. Excess acetic anhydride was quenched by addition of methanol (0.5 mL). The solvent was removed under reduced pressure and the residue was purified on a silica gel plate with 5% methanol/CHCl$_3$ as the developing solvent. The band at R$_f$0.55 afforded 0.026 g (0.09 mmol, 75%) of the title compound as a white solid: mp 158°–160° C. $^1$H NMR (Me$_2$SO-d$_6$) δ1.99 (s,3H),2.09(m,1H),2.61(m,1H),4.02–4.18,(m,5H),5.16(m,1H), 7.23(s,2H),8.13(s,1H),8.18(s,1H); UV(MeOH)-λ$_{max}$260 nm (ε10,668); mass spectrum,m/z 277 (,+).

EXAMPLE 8

2-(6-Amino-9H-purin-9-yl)-1,4-anhydro-2,3-dideoxy-D-arabinitol 5-H-Phosphonate

Representative Example

Salicylchlorophosphate (1M in dioxane, 0.24 mM) was added to a solution of 2-(6-amino-9H-purin-9-yl)-1,4-anhydro- 2,3-dideoxy-D-arabinitol (0.045 g, 0.191 mM) and triethylamine (0.27 mL, 1.91 mM) in dioxane (5mL). The resulting heterogeneous solution was allowed to stir for 1.5 h and was then quenched with water (5 mL). After stirring for an additional 10 minutes, the solution was neutralized, diluted with triethylammonium bicarbonate (0.5 M, 30 mL) and evaporated to dryness under reduced pressure. The crude product was then purified on DEAE-sephadex (A-25,0.0–0.5M triethylammonium bicarbonate gradient), sephadex-CM (Na$^+$form,H$_2$O eluant) and by reversed phase HPLC (Delta Pak C18, 10% E1OH/H$_2$O) to afford 0.043 g (70%) of the title compound: m.p. 232°–234° C.; UV (H20)λ$_{max}$259 nm (ε12,800); $^{31}$P NMR(DMSO-d$_6$) δ2.68 (dt,J=6.11,9.15 and 592 Hz); $^1$H NMR (DMSO-d$_6$) δ2.11 (m.1H),2.63(m,1H),3.83(m,2H),4.01(m,2H),4.11(m.1H), 5.17(m,1H), 6.62(d,1H,J=593 Hz),7.32(brs,2H),8.14(s,1H),8.27 (s,1H):$^{13}$C NMR (DMSO-d$_6$) δ34.1,53.8,64.2(d,J=4.88 Hz),71.7, 78.0,118.7,138.9,149.3,152.3,155.9.

EXAMPLE 9

1,4-Anhydro-3-α-azido-2,3-dideoxy-2-[3,4-dihydro-2,4-dioxo-5-methyl-1(2H)-pyrimidinyl]-D-arabinitol

Representative Example

To a solution of 1,4-anhydro-5-0-benzoyl-2-deoxy-2-[3,4-dihydro-2,4-dioxo-5-methyl-1(2H)-pyrimidinyl]-D-arabinitol 3-B-mesylate (0.040 g, 0.009 mmol), lithium azide (0.023 g, 0.48 mmol) in dry DMF (2mL) was heated at 100° C under a nitrogen atmosphere with stirring for 10 h. The volatiles were removed under reduced pressure, the residue partitioned between ethyl acetate (30 mL) and saturated aqueous sodium bicarbonate (10 mL) and washed with water (10 mL). The organic layer was dried (Na$_2$SO$_4$), filtered, and concentrated under reduced pressure. The residue was purified by preparative layer chromatography on silica gel with 6% methanol/chloroform as the developing solvent to afford the protected azido (0.029 g, 0.08 mmol, 81%) as a clear glass. A solution of the latter azido compound (0.029 g, 0.08 mmol) in methanolic ammonia (5 mL, saturated at 0° C.) was stirred at room temperature for 24 h. The volatiles were removed under reduced pressure and the residue was purified by preparative layer chromatography on silica gel with ethyl acetate/hexane as the developing solvent. The band at R$_f$0.41 was collected and further purified by reversed phase HPLC on Amberlite XAD-4 resin with 80:20 water/ethanol as the mobile phase. Lyophilization afforded the title compound (0.012 g, 0.045 mmol, 61%) as a white solid: mp 135°–138° C.; $^1$H NMR (Me$_2$SO-d$_6$) δ1.78 (s,3H), 3.60(m,3H),3.96(dd,1H;J=7.1,10.5 Hz),4.05(dd,1H;J=3.6, 10.5Hz),4.24(dd,1H;J=4.4,5.9 Hz),4.92(ddd,1H),5.05 (t,1H, exchangeable) 7.47(s,1H),9.74 (br s,1H,exchangeable); FTIR(KBr)2108(s), 1699(vs), 1696(s), 1653(m)cm$^{-1}$; UV(EtOH) λ$_{max}$269nm(ε9,300);[α]$_D$ =(+)30° (c=0.285, MeOH); mass spectrum,m/z 267 (M+).

EXAMPLE 10

Antiviral Activity 2-(6-Amino-9H-purin-9-yl)-1,4-anhydro-2,3-dideoxy-D-arabinitol of example 1 was tested for activity against HIV-1 in MT-4 cell lines in accordance with the procedure described by Mitsuya et al (*Proc. Natl. Acad. Sci.* 1985, 82 7096) and found to have activity against HIV-1 with E.D:$_{50}$ values at concentrations of 10–20 μM. 5-O-Acetyl-2-(6-amino-9H-purin-O-yl)-1,4-anhydro-2,3-dideoxy-D-arabinitol and 2-(6-amino-9H-purin-9-yl)-1,4-anhydro-2,3-dideoxy-D-arabinitol 5-H-phosphonate derivatives also showed similar anti-HIV activity.

What is claimed is:

1. 2'-isodideoxy-B-D-nucleosides of the formula I:

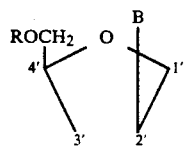

wherein the base moiety "B" or an acylated equivalent thereof is adenine, and wherein the "R" group is selected from hydrogen, acyl such as CH$_3$CO—phosphorylated groups such as H-phosphonate, and pharmaceutically acceptable salt forms thereof.

2. A composition of claim 1 wherein "R" =hydrogen.

3. A compound of claim 1, 2-(6-Amino-9H-purin-9-yl)-1,4 -anhydro-2,3-dideoxy-D-arabinitol.

4. A pharmaceutical composition comprising an effective nontoxic antiviral treating amount of the 2'-isodideoxy-B-D-nucleosides of formula I or the salts thereof:

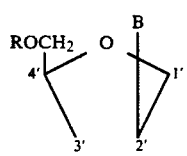

wherein the base moiety "B" or an acylated equivalent thereof is adenine, and wherein the "R" group is selected from hydrogen, acyl such as CH₃CO— phosphorylated groups such as H-phosphonate, and pharmaceutically acceptable salt forms thereof, and a pharmaceutically acceptable carrier.

5. The pharmaceutical composition of claim 4 which is in the form of an ointment or cream.

6. The pharmaceutical composition of claim 4 which is in the form of a tablet.

7. The pharmaceutical composition of claim 4 wherein the dosage amount is from about 1 to 250 mg per unit dose.

8. The composition of claim 4 wherein the formula (I) compound is 2-(6-Amino-9H-purin-9-yl)-1,4-anhydro-2,3-dideoxy-D-arabinitol.

* * * * *

UNITED STATES PATENT AND TRADEMARK OFFICE
CERTIFICATE OF CORRECTION

PATENT NO. : 5,231,174
DATED : 07/27/93
INVENTOR(S) : VASU NAIR

It is certified that error appears in the above-identified patent and that said Letters Patent is hereby corrected as shown below:

Column 2 line 51, -- a horizontal line should appear in the formula between line terminating adjacent to designation 3' and extending to the terminus of the lines crossing adjacent to 2'.

A similar line should extend between the like positions at approximately line 57 of column 2 and at approximately line 64 of column 2.

A similar horizontal line should extend between the point adjacent to the 3' position and the 2' position in claim 1 at approximately line 45, and also in claim 4 at approximately line 67.

Signed and Sealed this

Third Day of May, 1994

Attest:

BRUCE LEHMAN

Attesting Officer        Commissioner of Patents and Trademarks